United States Patent [19]

Tiep

[11] 4,190,876
[45] Feb. 26, 1980

[54] VARIABLE CAPACITORS

[75] Inventor: Brian L. Tiep, Monrovia, Calif.

[73] Assignee: City of Hope National Medical Center, Duarte, Calif.

[21] Appl. No.: 874,908

[22] Filed: Feb. 3, 1978

[51] Int. Cl.² .............................................. H01G 5/04
[52] U.S. Cl. .................................... 361/278; 361/277; 361/297
[58] Field of Search ............... 361/287, 290, 278, 297, 361/277

[56] References Cited

U.S. PATENT DOCUMENTS

| 1,715,319 | 5/1929 | Houck | 361/277 |
| 1,740,159 | 12/1929 | Dublier | 361/290 |
| 2,849,666 | 8/1958 | Seargeant | 361/287 |

FOREIGN PATENT DOCUMENTS

| 669076 | 11/1929 | France | 361/297 |
| 99051 | 6/1940 | Sweden | 361/297 |
| 207649 | 12/1923 | United Kingdom | 361/298 |
| 523888 | 7/1940 | United Kingdom | 361/297 |

*Primary Examiner*—E. A. Goldberg
*Attorney, Agent, or Firm*—Edward D. O'Brian

[57] ABSTRACT

A variable capacitor can be constructed so as to utilize two elongated metal strips serving as electrodes. Such strips are secured to one another so that at least a part of one is above at least a part of the other. The electrodes are insulated from one another and are disposed in a helical coil in which the turns are spaced from one another a sufficient extent to permit relative movement between the individual turns. In the disclosed capacitor a support or mounting collar is secured to the outermost turn and a movable actuator is secured to the innermost turn. Preferably at least one of the electrodes is sufficiently resilient so as to serve as a helical spring which will return the coil back to its initial configuration after at least one turn of the coil has been moved relative to an adjacent turn of the coil. A second collar may be located around the first and secured to the first by a flexible mounting structure such as a spring.

16 Claims, 3 Drawing Figures

VARIABLE CAPACITORS

CROSS-REFERENCE TO RELATED APPLICATIONS

The subject matter of this application is related to the subject matter of the co-pending Brian L. Tiep application entitled "METHOD OF MEASURING INTRATHORACIC PRESSURE", Ser. No. 874,909 filed Feb. 3, 1978 because the variable capacitors set forth herein are intended for use in connection with the method set forth in this co-pending application. The disclosure of this application is incorporated herein by reference.

BACKGROUND OF THE INVENTION

The invention set forth in this specification pertains to new and improved variable capacitors. More specifically it pertains to variable capacitors which can be effectively utilized in obtaining a measurement corresponding to intrathoracic pressure. It is considered, however, that the capacitors of the invention are capable of a wide variety of different, diverse uses.

A large number of different types of variable capacitors have been manufactured and sold. Normally such devices are constructed so that an electrode within such a capacitor may be moved relative to another electrode through the appropriate actuation of a mechanical element such as a shaft. On occasion such prior variable capacitors have been constructed so that one electrode is directly coupled to a mechanical actuator such as a rod used to transmit linear movement to the attached electrode. It will be recognized that this description of prior adjustable or variable capacitors is far from a complete description of all such known devices.

In spite of the fact that a large number of different types of adjustable or variable capacitors are known, it is considered that there is a need for new and improved variable capacitors which can be effectively utilized as transducers in monitoring relative movement of a member or object. More specifically it is considered there is a need for capacitors for such use which are comparatively simple to construct and yet which are of such a nature as to be highly responsive to relative movement so as to produce a variation in capacitance. It is also considered that there is a related need for variable capacitors as noted which are of such a character as to automatically return to an initial position after having been actuated by a physical force.

SUMMARY OF THE INVENTION

A broad objective of the present invention is to fulfill various needs as indicated in the preceding discussion. A related objective of the invention is to provide new and improved variable capacitors: which are not particularly difficult to construct; which can be manufactured at a comparatively nominal cost; which can be satisfactorily utilized as transducers in applications such as in measuring tension changes relfecting intrathoracic pressure; and which are of such a character that they will automatically return to an initial adjustment or position after having been activated by a physical force.

In accordance with this invention these objectives are achieved by providing a capacitor having two electrodes which are separated from one another in which the improvement comprises: both of the electrodes comprising elongated, electrically conducting strips having sides, top and bottom edges and ends; dielectric means for electrically isolating the electrodes from one another and for holding the electrodes together, the dielectric means securing the electrodes together along their lengths so that the top edge of one of the electrodes is adjacent to the bottom edge of the other of the electrodes, so that the electrodes are oriented vertically with respect to one another and so that at least some portions of the sides of the electrodes do not overlap one another, the electrodes and the dielectric means being disposed in a helical coil in which the turns are spaced from one another to a sufficient extent to permit relative movement between at least some adjacent turns in a direction which is axial relative to the axis of the coil, the electrodes in the dielectric means being sufficiently flexible so as to permit such relative movement between at least two adjacent turns of the coil.

In a presently preferred capacitor as indicated in the preceding paragraph at least one of the electrodes is sufficiently resilient so as to serve as a helical spring which will return to its initial configuration after at least one adjacent turn of the coil has been moved relative to another adjacent turn of the coil. In the capacitor disclosed the outermost turn of the coil is secured to a collar serving as a holding means for mounting the capacitor while an actuator serving as an adjustment means is secured to the center turn of the coil for use in physically moving at least one turn of the coil so as to vary the capacitance of the coil.

BRIEF DESCRIPTION OF THE DRAWING

Because of the nature of the invention it is best more fully described with reference to the accompanying drawing in which.

Figure 1:
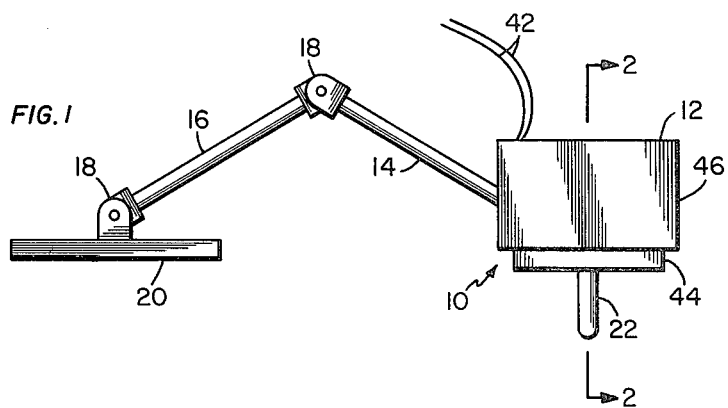
FIG. 1 is a side elevational view of a presently preferred form or embodiment of a variable capacitor in accordance with this invention.
Figure 2:
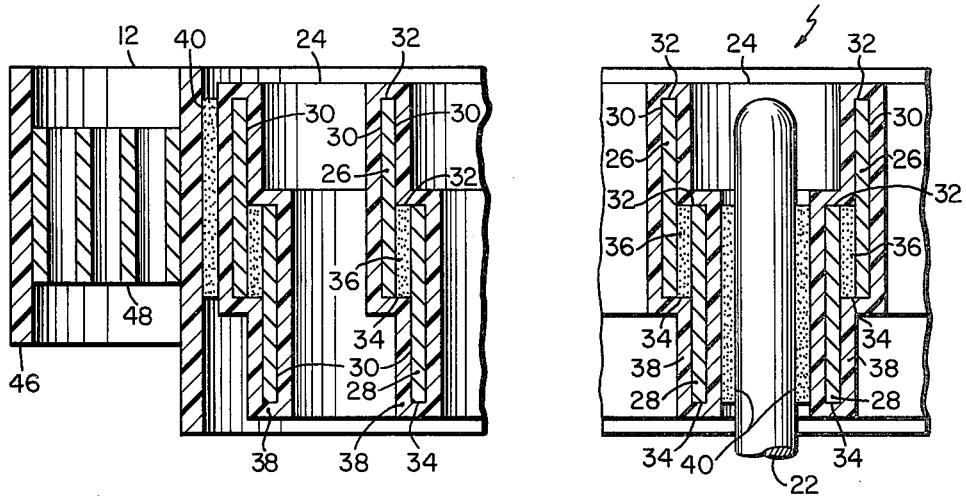
FIG. 2 is a partial cross-sectional view at an enlarged scale taken at line 2—2 of FIG. 1.

The particular capacitors illustrated are constructed so as to utilize the concepts or principles verbally defined in the appended claims. Those skilled in the art of constructing variable capacitors will realize that these concepts or principles can be embodied in other variable capacitors which differ from the precise capacitors illustrated as to various matters within the scope of routine engineering modification.

DETAILED DESCRIPTION

In the drawing there is shown a variable capacitor 10 of the present invention which includes a collar 12 as hereinafter described used to support the various elements of the capacitor 10 hereinafter separately described. This collar 12 is rigidly attached to an arm 14 which in turn is secured to another arm 16 through the use of a conventional universal joint 18. A similar universal joint 18 is utilized to secure the arm 16 to a plate 20 used to support the entire capacitor 10 as it is employed for its intended utilization.

The plate 20 is preferably shaped so as to be capable of being secured to the skin of a human immediately adjacent to the sternum when the capacitor 10 is employed in its presently preferred utilization. The plate 20 may be secured in such a location in various conventional ways such as, for example, through the use of adhesive tape. When it is secured in place the iniversal joints 18 frictionally hold the arms 14 and 16 so that the collar 12 is located in such a manner that the position of the capacitor 10 can be adjusted.

The purpose of such adjustment in the preferred utilization of the capacitor 10 is to position a rigid actuator 22 extending beneath the collar 12 against the soft tissue immediately above the supra sternal notch of an individual which is located toward the head from the pleural notch. When the capacitor 10 is used in this manner pressure will be exerted on the actuator 22 so as to tend to move this actuator 22 in accordance with body movement in the area of the body contacted by the actuator 22. Such movement will be transmitted by the actuator 22 to the innermost turn (not separately numbered) of a helical coil 24. Such a coil 24 may be referred to as a flat, spiral coil.

This coil 24 is constructed so as to include two electrodes 26 and 28. Each of these electrodes 26 and 28 is an elongated, electrically conductive strip having sides 30, a top edge 32 and a bottom edge 34. These electrodes 26 and 28 have ends (not separately indicated) which are co-terminous at the ends of the coil 24. The electrodes 26 and 28 are located parallel to one another so that a side 30 of the electrode 26 adjacent to the bottom edge 34 of the electrode 26 overlaps a side 30 of the electrode 28 adjacent to the top edge 32 of the electrode 28.

The adjacent overlapping portions (not separately numbered) of the sides 30 of the electrodes 26 and 28 are secured together by means of an electrically nonconductive or dielectric adhesive 36 serving to secure these electrodes 26 and 28 together as a unit. Preferably all of the exposed sides 30 and edges 32 and 34 of the electrodes 26 and 28 are covered by a coating 38 of a dielectric material. This coating 38 is preferably employed in order to guard against the possibility of adjacent turns (not separately numbered) of the coil 28 coming in contact with one another so as to result in direct electrical contact between the electrode 26 and the electrode 28.

As indicated in the preceding the innermost turn (not separately numbered) of the coil 24 is directly secured to the actuator 22. An adhesive 40 may conveniently be employed for this purpose although, of course, other mechanically equivalents may be employed. Similarly the outermost turn of the coil 24 may be attached to the interior of the collar 12 by a mechanical means such as a similar adhesive 40 so that the periphery of the coil 24 is held by the collar 12. In order to complete the unit, wires 42 are attached to the electrodes 26 and 28 adjacent to the collar 12 so as to lead from the capacitor 10.

It is considered important that the individual turns (not separately numbered) of the coil 24 be spaced sufficiently far from one another so as to permit relative movement between adjacent turns of this coil 24 in a direction which is axial relative to the axis of the coil 24. In the illustrated unit the actuator 22 extends axially with respect to this coil 24. When this actuator 22 is moved, it in effect "adjusts" the coil 24 so as to vary the positions of at least two adjacent turns of this coil 24 so that the coil 24 does not extend in a substantially flat plane but instead assumes a somewhat conical type of configuration. As this occurs the relative spacing and/or overlap between the electrodes 26 and 28 will be varied and this, of course, will result in the variation in the capacitance of the capacitor 10. When the actuator 22 is moved back to its original position the capacitor 10 will, of course, have its original capacitance.

In order to achieve this mode of operation it is necessary that the electrodes 26 and 28, the adhesive 36 and the coating 38 be sufficiently flexible so as to permit relative movement as described within the coil 24. It is considered preferable to form at least one of the electrodes 26 and 28 of a material which, in addition to being flexible as indicated, is also sufficiently resilient so as to serve as a helical spring which, when released, will return to its initial configuration. As an example of this, one of the electrodes 26 and 28 can be formed out of spring steel while the other of the electrodes 26 and 28 is formed of a less resilient material such as copper. If desired, both of the electrodes 26 and 28 can be formed out of spring steel, although this is not considered necessary for the entire coil 24 to in effect constitute a helical spring which will return to its initial configuration after mechanical force has been applied so as to move individual turns in the coil from their initial configuration.

This use of at least one electrode 26 and 28 which has the character of a spring is considered advantageous because it makes the capacitor 10 of such a nature that the capacitor 10 will automatically return to its initial adjustment or position when a mechanical force is no longer applied to it. This is accomplished in the capacitor 10 without the use of a separate external spring. Further the use of an electrode 26 or 28 which is in fact a spring makes it possible to utilize the capacitor 10 so that the actuator 22 applies a consistent pressure such as to the area of the body noted in the preceding. This is considered to be desirable in connection with the intended utilization of the invention in obtaining a measurement corresponding to intrathoracic pressure. The collar 12 employed in the capacitor 10 may be a completely rigid collar. While this may be desirable for some utilizations of the capacitor 10 it is considered preferable to form this collar 12 so that in effect it consists of inner and outer rigid collars 44 and 46 which are connected together by a second, comparatively weak helical spring 48. This structure of the collar 12 in effect mounts the entire coil 24 and the actuator 22 in such a manner as to provide what may be regarded as a flexible or almost gimbal-like mounting for the coil 24 and the actuator 22.

Such a mounting is considered preferable in connection with the use of the capacitor 10 so that the actuator 22 is located in order to resiliently bias against the soft tissue immediately above the super sternal notch of an individual as indicated in the preceding. With this preferred construction the inner collar 44, the coil 24, and the actuator 22 can move to a slight or limited amount so as to accommodate other than "in" or "out" or lateral skin and/or body changes in position which do not accurately reflect the measurements being obtained through the movement of the actuator 22. On some occasions it is considered that it may be preferable to actually locate the collar 12 so that the inner collar 44 directly bears against the body in the area of the super sternal notch of an individual while the actuator 22 is used as described in the preceding.

Figure 3:
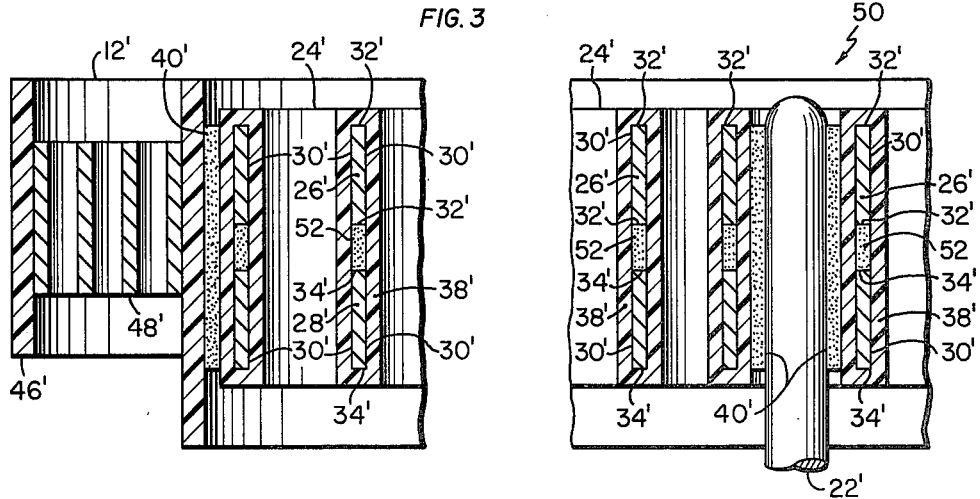
FIG. 3 is a cross-sectional view corresponding to FIG. 2 of a modified variable capacitor which is quite similar to the capacitor illustrated in the preceding figures.

In FIG. 3 of the drawing there is indicated a capacitor 50 which is quite similar to the capacitor 10 described in the preceding. Because of the close similarity between the capacitors 10 and 50 the various parts of the capacitor 50 are not separately described herein and are designated in the drawing and, where necessary for explanatory purposes, in the remainder of this specification by the primes of the numerals previously utilized to designate such parts.

The sole difference between the capacitors 10 and 50 relates to the fact that in the capacitor 10 the electrodes 26 and 28 are located so as to overlap one another as described in the preceding whereas in the capacitor 50 the electrodes 26' and 28' are located so as to be coplanar with one another—i.e., so as to be located directly above one another. In the capacitor 50 a small dielectric strip 52 is located between the lower edge 34' of the electrode 26' and the upper edge 32' of the lowermost electrode 28'. This strip 52 is preferably of an adhesive character so as to bond the edges of the two electrodes 26' and 28' together in the orientation described. The coating 38' used in the capacitor 50 preferably is sufficiently thick as to possess mechanical properties serving to aid in holding the electrodes 26' and 28' together.

I claim:

1. A capacitor having two electrodes which are separated from one another in which the improvement comprises:
   both of said electrodes comprising elongated, electrically conductive strips having sides, top and bottom edges, and ends,
   dielectric means securing said electrodes together along their lengths so that the top edge of one of said electrodes is adjacent to the bottom edge of the other of said electrodes so that said electrodes are oriented vertically with respect to one another, and so that at least some portions of the sides of said electrodes do not overlap one another,
   said electrodes and said dielectric means being disposed in a helical coil in which the turns are spaced outwardly from the axis of the coil from one another to a sufficient extent so as to permit relative movement between at least some adjacent turns in a direction which is axial relative to the axis of said coil,
   said electrodes and said dielectric means being sufficiently flexible so as to permit such relative movement between at least two adjacent turns of said coil.

2. A capacitor as claimed in claim 1 wherein:
   at least one of said electrodes is sufficiently resilient so as to serve as a helical spring which will return to its initial configuration after at least one adjacent turn of said coil has been moved relative to another adjacent turn of said coil.

3. A capacitor as claimed in claim 1 including:
   other dielectric means covering the sides of said electrodes so that as a turn of said coil is moved relative to another turn of said coil in a direction which is axial relative to the axis of said coil said electrodes remain electrically isolated from one another.

4. A capacitor as claimed in claim 1 wherein:
   a portion of a side of the lowermost of said electrodes adjacent to the top edge thereof is overlapped by a portion of a side of the uppermost of said electrodes adjacent to the lower edge thereof.

5. A capacitor as claimed in claim 4 wherein:
   at least one of said electrodes is sufficiently resilient so as to serve as a helical spring which will return to its initial configuration after at least one adjacent turn of said coil has been moved relative to another adjacent turn of said coil, and including
   other dielectric means covering the sides of said electrodes so that as a turn of said coil is moved relative to another turn of said coil in a direction which is axial relative to the axis of said coil said electrodes remain electrically isolated from one another.

6. A capacitor as claimed in claim 5 including:
   holding means for use in mounting the capacitor secured to the outermost of said turns of said coil, and
   adjustment means for use in physically moving at least one turn of said coil so as to vary the capacitance of said capacitor secured to the center turn of said coil.

7. A capacitor as claimed in claim 6 wherein:
   said holding means comprises a collar structure located around and secured to the outermost of said turns of said coil.

8. A capacitor as claimed in claim 7 wherein:
   said collar structure includes concentric, rigid inner and outer collars, the inner of said collars being secured to the outermost of said turns of said coil and includes gimbal means connecting said collars.

9. A capacitor as claimed in claim 8 wherein:
   said gimbal means comprises a helical spring, 10. A capacitor as claimed in claim 1 wherein:
    said electrodes are located one above another with the upper edge of the lowermost of said electrodes being adjacent to the lower edge of the uppermost of said electrodes.

11. A capacitor as claimed in claim 10 wherein:
    at least one of said electrodes is sufficiently resilient so as to serve as a helical spring which will return to its initial configuration after at least one adjacent turn of said coil has been moved relative to another adjacent turn of said coil, and including
    other dielectric means covering the sides of said electrodes so that as a turn of said coil is moved relative to another turn of said coil in a direction which is axial relative to the axis of said coil said electrodes remain electrically isolated from one another.

12. A capacitor as claimed in claim 11 including:
    holding means for use in mounting the capacitor secured to the outermost of said turns of said coil, and
    adjustment means for use in physically moving at least one turn of said coil so as to vary the capacitance of said capacitor secured to the center turn of said coil.

13. A capacitor as claimed in claim 1 including:
    holding means for use in mounting the capacitor secured to the outermost of said turns of said coil, and
    adjustment means for use in physically moving at least one turn of said coil so as to vary the capacitance of said capacitor secured to the center turn of said coil.

14. A capacitor as claimed in claim 13 wherein:
    said holding means comprises a collar structure located around and secured to the outermost of said turns of said coil.

15. A capacitor as claimed in claim 14 wherein:
    said collar structure includes concentric, rigid inner and outer collars, the inner of said collars being secured to the outermost of said turns of said coil and includes gimbal means connecting said collars.

16. A capacitor as claimed in claim 15 wherein:
    said gimbal means comprises a helical spring.

* * * * *